(12) United States Patent
Guzman (10) Patent No.: US 10,105,289 B2
(45) Date of Patent: Oct. 23, 2018

(54) BIOMIMETIC MINERAL BASED ENDODONTIC CEMENT COMPOSITION AND USES THEREOF

(71) Applicant: Essential Dental Systems, Inc., South Hackensack, NJ (US)

(72) Inventor: Jason Edward Guzman, Union City, NJ (US)

(73) Assignee: ESSENTIAL DENTAL SYSTEMS, INC., South Hackensack, NJ (US)

( * ) Notice: Subject to any disclaimer, the term of this patent is extended or adjusted under 35 U.S.C. 154(b) by 0 days.

(21) Appl. No.: 15/590,931

(22) Filed: May 9, 2017

(65) Prior Publication Data

US 2017/0340523 A1   Nov. 30, 2017

Related U.S. Application Data

(60) Provisional application No. 62/342,139, filed on May 26, 2016.

(51) Int. Cl.
| | |
|---|---|
| *A61K 9/00* | (2006.01) |
| *A61K 6/06* | (2006.01) |
| *A61K 6/00* | (2006.01) |
| *A61K 6/087* | (2006.01) |
| *A61K 6/027* | (2006.01) |
| *A61K 6/083* | (2006.01) |

(52) U.S. Cl.
CPC ............ *A61K 6/0643* (2013.01); *A61K 6/002* (2013.01); *A61K 6/0035* (2013.01); *A61K 6/0038* (2013.01); *A61K 6/0067* (2013.01); *A61K 6/0276* (2013.01); *A61K 6/0681* (2013.01); *A61K 6/083* (2013.01); *A61K 6/087* (2013.01)

(58) Field of Classification Search
CPC ...................................................... A61K 6/643
See application file for complete search history.

(56) References Cited

U.S. PATENT DOCUMENTS

| | | |
|---|---|---|
| 6,387,981 B1 | 5/2002 | Zhang et al. |
| 7,214,726 B2 | 5/2007 | Qian |
| 7,361,216 B2 | 4/2008 | Kangas et al. |
| 7,575,628 B2 | 8/2009 | Lu et al. |
| 7,619,016 B2 | 11/2009 | Dickens et al. |
| 7,649,029 B2 | 1/2010 | Kolb et al. |

(Continued)

FOREIGN PATENT DOCUMENTS

| | | |
|---|---|---|
| JP | 2009183548 A | 8/2009 |
| WO | 2005087178 A1 | 9/2005 |

OTHER PUBLICATIONS

Invitation to Pay Additional Fees, and, Where Applicable, Protest Fees mailed Jul. 24, 2017, issued in connection with corresponding International Application No. PCT/US17/32068 (2 pages total).
Komabayashi, et al., "Current Status Of Direct Pulp-Capping Materials for Permanent Teeth", Dent Mater J. Jan. 31, 2016; 35(1): 1-12 (13 pages total).

(Continued)

*Primary Examiner* — Paul W Dickinson
(74) *Attorney, Agent, or Firm* — Maldjian Law Group LLC (57) ABSTRACT

Disclosed are biomimetic mineral based endodontic cement compositions. An endodontic cement comprises a paste A and a paste B. The paste A comprises a pozzolanic cementitious mineral paste and the paste B is a mixture comprising polyanionic polymers, phosphates, cement setting modulators, host-inclusion particles, bioactive glasses, and radiopacity agents suspended in a liquid carrier.

21 Claims, 3 Drawing Sheets

(56) References Cited

U.S. PATENT DOCUMENTS

| | | | |
|---|---|---|---|
| 7,942,961 B2 | 5/2011 | Asgary | |
| 7,947,759 B2 | 5/2011 | Lin et al. | |
| 8,183,306 B2 | 5/2012 | Kohro | |
| 8,343,271 B1 | 1/2013 | Lu et al. | |
| 8,475,811 B2 | 7/2013 | Yang et al. | |
| 8,557,038 B2 | 10/2013 | Chow et al. | |
| 8,658,712 B2 | 2/2014 | Primus et al. | |
| 8,741,268 B2 | 6/2014 | Peterson | |
| 8,889,196 B2 | 11/2014 | Xu | |
| 9,101,436 B2 | 8/2015 | Chow et al. | |
| 2005/0028705 A1 | 2/2005 | Wagh et al. | |
| 2008/0160091 A1 | 7/2008 | Kropf et al. | |
| 2010/0010115 A1* | 1/2010 | Kohro | A61K 6/083 523/116 |
| 2010/0260849 A1 | 10/2010 | Rusin et al. | |
| 2011/0053117 A1 | 3/2011 | Engelbrecht et al. | |
| 2013/0066324 A1 | 3/2013 | Engqvvist et al. | |
| 2015/0183687 A1 | 7/2015 | Engqvvist et al. | |

OTHER PUBLICATIONS

International Search Report and Written Opinion dated Oct. 2, 2017, which issued in connection with corresponding International Application No. PCT/US17/32068 (12 pages total).

Cao et al., "Methods for Biomimetic Remineralization of Human Dentine: A Systematic Review", International Journal of Molecular Sciences, vol. 16, Issue 3, Mar. 2, 2015, retrieved on Mar. 21, 2017 from http://www.mdpi.com/1422-0067/16/3/4615/htm, pp. 4615-4627.

Gandolfi et al., "Biomimetic Remineralization of Human Dentin Using Promising Innovative Calcium-Silicate Hybrid "Smart" Materials", Dental Materials, vol. 27, Issue 11, Nov. 2011, pp. 1055-1069.

Padovani et al., "Advances in Dental Materials through Nanotechnology: Facts, Perspectives and Toxicological Aspects", Trends in Biotechnology, vol. 33, No. 11, Nov. 2015, pp. 621-636.

Jefferies, "Bioactive and Biomimetic Restorative Materials: A Comprehensive Review. Part II", Journal of Esthetic and Restorative Dentistry, vol. 26, Issue 1, 2014, pp. 27-39.

* cited by examiner

BIOMIMETIC MINERAL BASED ENDODONTIC CEMENT COMPOSITION AND USES THEREOF

CROSS REFERENCE TO RELATED APPLICATIONS

This application claims priority to, and the benefit of, Provisional Application No. 62/342,139 filed May 26, 2016, the entirety of which is incorporated by reference herein.

BACKGROUND

Field

Embodiments of the present invention generally relate to a mineral and matrix based cement composition for biomedical applications, and particularly to a biomimetic remineralizing mineral based cement composition for dental applications.

Description of Related Art

Root canal therapy has been in use for decades and is one of the most effective and preferred procedures for retaining teeth that have been compromised by severe decay or structural problems affecting the pulp tissues. In fact, root canal therapy or an endodontic therapy, is often preferred over a dental implant as the costs of dental implants are often significantly higher than other treatments. However, the average life time of a root canal filling of a tooth is approximately ten years, during which time the treated tooth incurs demineralization and decay due to the re-infiltration of bacteria which produces metabolic byproducts such as, acids, which, over time, decays the treated tooth. Similarly, the life span of other dental restorations are adversely affected by bacteria as well.

Various premixed cementitious compositions including primarily calcium silicates, have been used for endodontic applications. However, these compositions possess only passive remineralizing properties and, once placed and set, no longer continue to reinforce the remaining tooth structure or protect against re-infiltration of bacteria in the treated tooth. Certain remineralizing cementitious compositions have also been used for dental applications, particularly, in endodontic therapy. However, these remineralizing compositions do not actively induce remineralization nor do they provide sustained disinfection or prophylaxis required for reinforcement and preservation of endodontically treated teeth.

There remains a need for endodontic treatments that have extended life, actively induce remineralization, and have prolonged anti-microbial properties.

SUMMARY

Embodiments in accordance with the present invention provide a biomimetic mineral based endodontic cement composition, including, a paste A and a paste B, wherein the paste A is a pozzolanic cementitious mineral paste and the paste B is a mixture including phosphates, polyanionic polymers, cement setting modulators, host-inclusion particles, bioactive glasses, and radiopacity agents suspended in a non-aqueous liquid carrier.

Embodiments in accordance with the present invention provide a biomimetic mineral based endodontic cement composition, including a paste A and a paste B, with a syringe having one or more barrels and a mixing tip, wherein the paste A and paste B are mixed together upon extrusion through the mixing tip, wherein the paste A is a pozzolanic cementitious mineral paste and the paste B is a mixture comprising phosphates, polyanionic polymers, cement setting modulators, host-inclusion particles, bioactive glasses, and radiopacity agents suspended in a non-aqueous liquid carrier.

Embodiments in accordance with the present invention provide a method of preparing a biomimetic mineral based endodontic cement composition. The method comprises mixing of a paste A and a paste B, wherein the paste A is a pozzolanic cementitious mineral paste and the paste B is a mixture comprising phosphates polyanionic polymers, cement setting modulators, host-inclusion particles, bioactive glasses, and radiopacity agents suspended in a non-aqueous liquid carrier.

Embodiments in accordance with the present invention provide a biomimetic mineral based endodontic cement composition that actively mimics naturally-biologically occurring remineralizing mechanisms in developing dentition/teeth.

Embodiments in accordance with the present invention provide a biomimetic mineral based endodontic cement composition that provides sustained disinfection or prophylaxis and remineralization of the dentition/teeth.

Embodiments in accordance with the present invention provide a biomimetic mineral based endodontic cement composition which enhances the lifetime of a root canal and/or dental restoration.

These and other advantages will be apparent from the present application of the embodiments described herein.

The preceding is a simplified summary to provide an understanding of some embodiments of the present invention. This summary is neither an extensive nor exhaustive overview of the present invention and its various embodiments. The summary presents selected concepts of the embodiments of the present invention in a simplified form as an introduction to the more detailed description presented below. As will be appreciated, other embodiments of the present invention are possible utilizing, alone or in combination, one or more of the features set forth above or described in detail below.

BRIEF DESCRIPTION OF THE DRAWINGS

The foregoing and other aspects of the embodiments disclosed herein are best understood from the following detailed description when read in connection with the accompanying drawings. For the purpose of illustrating the embodiments disclosed herein, there is shown in the drawings embodiments presently preferred, it being understood, however, the embodiments disclosed herein are not limited to the specific instrumentalities disclosed. Included in the drawings are the following figures.

While embodiments of the present invention are described herein by way of example using several illustrative drawings, those skilled in the art will recognize the present invention is not limited to the embodiments or drawings described. It should be understood the drawings and the detailed description thereto are not intended to limit the present invention to the particular form disclosed, but to the contrary, the present invention is to cover all modification, equivalents and alternatives falling within the spirit and scope of embodiments of the present invention as defined by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

Embodiments of the present invention will be illustrated below in conjunction with exemplary compositions or formulations of the biomimetic mineral based endodontic cement composition.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "endodontic", as used herein, refers to a branch of dentistry related to diseases of dental pulp, and can be used interchangeably with "dental" in the present application.

The term "biomimetic", as used herein, refers to substances, or processes that imitates any naturally occurring biological process or function of any naturally occurring biological compound.

The term "dental restoration", as used herein, refers to any restorative material, or structure used for restoring a function, integrity and morphology of missing, dysfunctional or damaged tooth structure.

The term "pozzolanic", as used herein, refers to siliceous (calcium silicates, dicalcium silicate, tricalcium silicate) and aluminous, aluminosilicate (metakaolin) and/or reactive magnesia materials which, in finely divided form and in the presence of water, chemically react with alkali phosphates to form materials with cementitious properties.

The term "radiopacity", as used herein, refers to materials which are opaque to X-rays.

The term "antimicrobial", as used herein, refers to materials and compounds which either prevent microbial colonization, or are biocidal to microbes. The term includes compounds such as:

The term "host-inclusion particles", as used herein, refers to non-reactive porous and/or tubular materials capable of attaching, adhering, or being impregnated with other smaller compounds (e.g., antimicrobial agents, remineralizing agents, etc.).

In an embodiment of the present invention, the endodontic cement composition, comprising a Paste A and a Paste B is provided, wherein the paste A is an alkaline pozzolanic cementitious mineral paste and the Paste B is an acidic mixture comprising polyanionic polymers, cement setting modulators, wherein either paste A or paste B may include host-inclusion particles, bioactive glasses, and radiopacity agents suspended in a non-aqueous carrier.

The biomimetic mineral based endodontic cement composition is referred to herein as endodontic cement composition.

In an embodiment of the present invention, other additives (reactive and non-reactive, or medically active) may be included in the endodontic cement composition, as desired for or required by any particular biomedical application.

In an embodiment of the present invention, the Paste A is an alkaline, pozzolanic cementitious mineral paste comprising a blend of reactive magnesia, calcium hydroxide, and calcined clays, and/or hydroxyapatite nanopowders suspended in a non-aqueous hydrophilic non-aqueous carrier.

In an embodiment of the present invention, the Paste A is an alkaline, pozzolanic cementitious mineral paste comprising a blend of pozzolanic cementitious material, calcium hydroxide, sodium borate, and magnesium oxide, sodium phosphate, potassium phosphate, ammonium phosphate and/or calcium oxide suspended in a non-aqueous liquid carrier.

In an embodiment of the present invention, the Paste A is a pozzolanic cementitious mineral paste comprising a blend of pozzolanic cementitious material, calcium hydroxide, sodium borate, calcium chloride, magnesium oxide, sodium phosphate, potassium phosphate, ammonium phosphate and/or calcium oxide, antimicrobial agents, host-inclusion powders, and radiopacity agents suspended in a non-aqueous liquid carrier.

In an embodiment of the present invention, the Paste A is a pozzolanic cementitious mineral paste comprising a blend of pozzolanic cementitious material, calcium hydroxide, magnesium oxide and/or calcium oxide, magnesium oxide calcined, bioactive glass, halloysite clay, halloysite clay/chlorohexidine/benzalkonium chloride/benzethonium chloride, hydroxyapatite nanopowder, and radiopacity agents suspended in a liquid carrier. Magnesium oxide is known to enhance osteoclast and osteoblast activity and has no known adverse effect as the magnesium is released into the bone. Furthermore, where magnesium oxide is calcined, non-reactivity is increased, and is thus preferable in some embodiments.

In an embodiment of the present invention, the pozzolanic cementitious material can include, but not restricted to, diatomaceous earth, pumice, meta-kaolin, and the like, or combinations thereof.

In an embodiment of the present invention, the host-inclusion particles of either Paste A or Paste B can include, but not restricted to, mesoporous silica, silver nanoparticles, metal oxide nanoparticles, cross-linked quaternary ammonium polyethylenimine (QPEI) nanoparticles halloysite clay, aluminum silicate, and the like, or combinations thereof.

Figure 1:
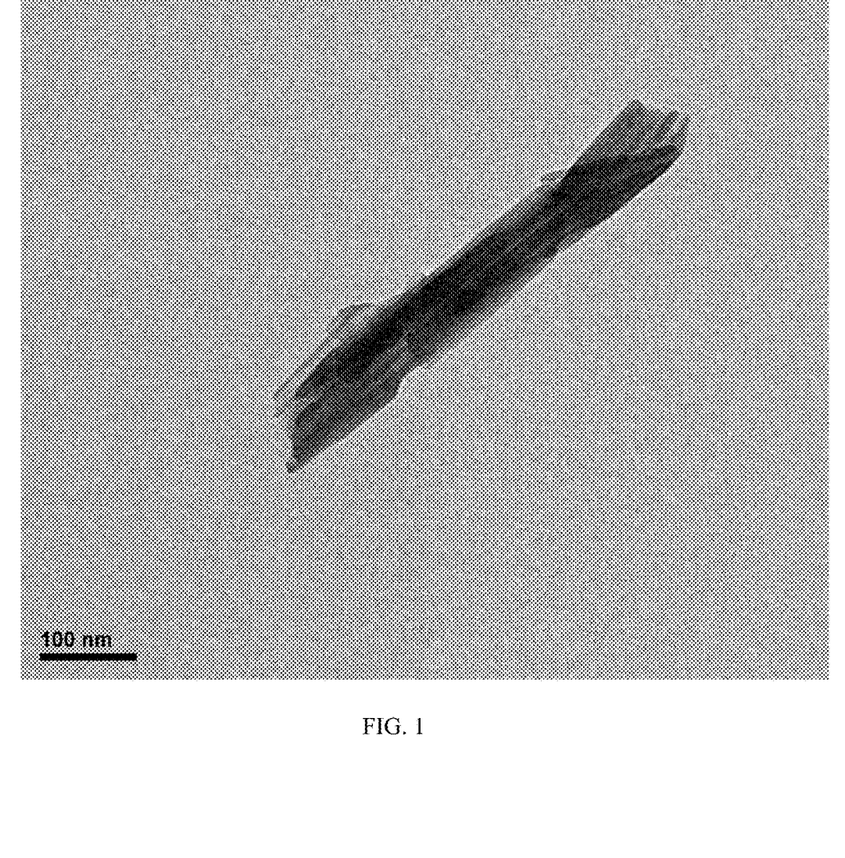
FIG. 1 is a transmission electron microscopy image of halloysite clay nanotubes, as in one embodiment of the present invention.
Figure 2:
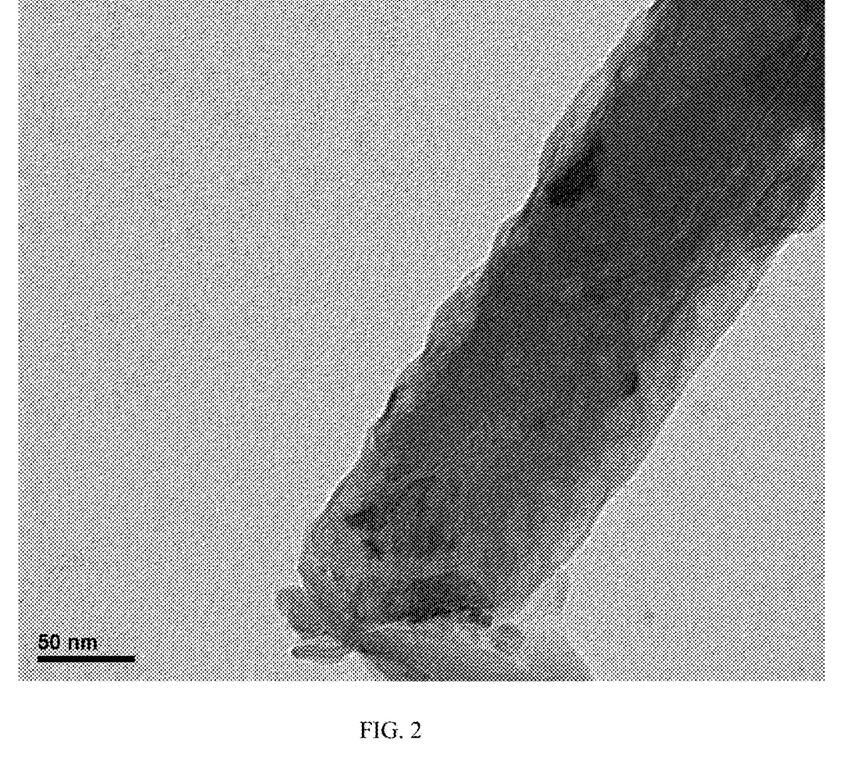
FIG. 2 is a transmission electron microscopy image of halloysite clay nanotubes with chlorohexidine adhered to the interior and exterior of the nanotube, as in one embodiment of the present invention.

As seen in FIG. 1, halloysite clay comprises a plurality of nanotubes in an unaltered state. By following protocols to those known in the art, the halloysite clay can be loaded with compound to deliver desired compounds to the target area. FIG. 2 shows halloysite clay loaded with chlorohexidine, an antimicrobial agent. As is apparent, compound adheres to both the inner and outer portions of the halloysite nanotubes. In some preferred embodiments, the halloysite clay is loaded with antimicrobial agents which are released from the endodontically treated tooth over a period of time (i.e., months or years), to achieve a sustained antimicrobial effect.

In an embodiment of the present invention, the host-inclusion particles may be loaded with antimicrobial or antibacterial agents, wherein the antimicrobial or antibacterial agents can include, but not restricted to, silver oxide, titanium oxide, bioactive glass, zirconium oxide, chlorohexidine, benzalkonium chloride, benzethonium chloride, and the like, or combinations thereof.

In some embodiments of the present invention, the nanotubes of the halloysite clay are impregnated with antimicrobial agents such as titanium oxide, chlorohexidine, benzalkonium chloride, benzethonium chloride, or combinations thereof.

In an embodiment of the present invention, the host-inclusion particles may be loaded with remineralizing agents, which remineralizing agents in paste A passively induce remineralization, and in paste B actively induced remineralization. The remineralizing agents may include, but not be restricted to, calcium silicates, magnesium oxide, calcium phosphate, hydroxyapatite, polyanionic polymers, and the like, or combinations thereof. In those embodiments, the hydroxyapatite serves to initiate the remineralizing capacity of the set material. Paste A and paste B are loaded into separate barrels and administered in combination. This combination composition of paste A and paste B actively induces remineralization (biomimetic polymers) over an extended period of time as well as provides long term prophylaxis.

In an embodiment of the present invention, the remineralizing and antimicrobial or antibacterial agents diffuse from the host-inclusion particles and aids in sustained disinfection or prophylaxis and remineralization of the surrounding dentition resulting in reinforcement of the treated tooth.

In an embodiment of the present invention, the bioactive glass can include, but not restricted to, Bioactive glass 45S5 (original bioglass), bioactive glass 58S, bioactive glass S53P54, the like, and combinations thereof.

Figure 3:
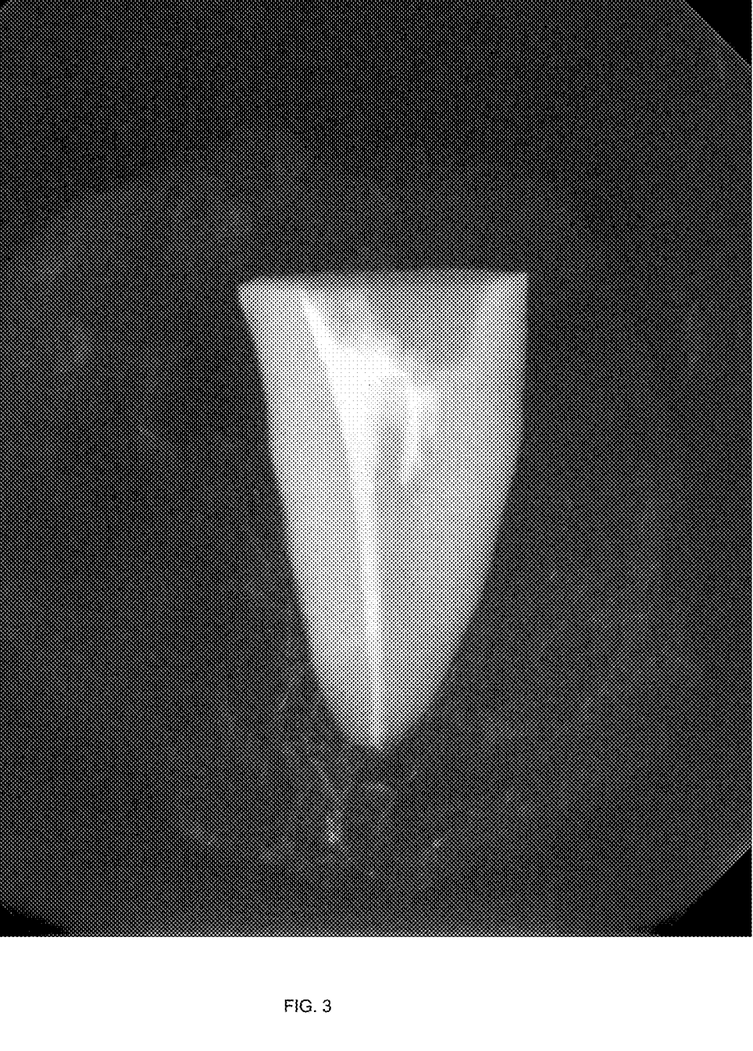
FIG. 3 is an x-ray image of a tooth treated with the endodontic cement demonstrating radiopacity, as in one embodiment of the present invention.

In an embodiment of the present invention, the radiopacity agents if either Paste A or Paste B can include, but not restricted to, bismuth oxide, zinc oxide, lead oxide, bismuth subnitrate, bismuth carbonate, barium sulfate, calcium tungstate, and zirconium oxide, niobium oxide, ytterbium trifluoride, and the like, or combinations thereof. The radiopacity agents allow for viewing of the composition as placed within the endodontically treated tooth, as illustrated by FIG. 3.

In an embodiment of the present invention, the liquid carrier or either Paste A or Paste B can include an ionic liquid, a non-aqueous hydrophilic solvent, and combinations thereof. The ionic liquid can include, but not restricted to, tetrafluoroborates such as 1-Butyl-3-methylimidazolium tetrafluoroborate (BMim$^+$ BF4), and the like, or combinations thereof. The ionic liquid aids in catalyzing the biomimetic remineralization reaction. The non-aqueous liquid can include, but not restricted to, glycerol, glycerin, polyethylene glycol, dimethyl sulfoxide (DMSO), and the like, or combinations thereof. In some preferred embodiments, the liquid carrier is polyethylene glycol of 300 MW, other molecular weights are contemplated and do not depart from the scope of the invention.

In an exemplary scenario, the Paste A (Paste A1) comprises about 15-25% by weight pozzolanic cementitious material (calcium silicates, metakaolin, or magnesium oxide), about 1-5% by weight calcium hydroxide, about 25-45% by weight ytterbium trifluoride and/or niobium oxide, about 0.5-20% by weight magnesium oxide and/or calcium oxide, and about 25-50% by weight 1-Butyl-3-methylimidazolium tetrafluoroborate (Bmim$^+$ BF4$^-$).

In an exemplary scenario, the Paste A (Paste A2) comprises about 15-25% by weight pozzolanic cementitious material, about 1-5% by weight calcium hydroxide, about 25-45% by weight ytterbium trifluoride and/or niobium oxide, about 0.5-7% by weight magnesium oxide and/or calcium oxide, and about 25-50% by weight dimethyl sulfoxide (DMSO).

In another exemplary scenario, the Paste A (Paste A3) comprises about 25% by weight magnesium oxide calcined (heat treated) by weight, 0.1-1% by weight calcium hydroxide, 50% by weight zirconium oxide, and 25% by weight polyethylene glycol (300 MW).

In yet another exemplary scenario, the Paste A (Paste A4) comprises about 25% by weight magnesium oxide calcined (heat treated) by weight, 0.1-1% by weight calcium hydroxide, 48-49.9% by weight zirconium oxide, 25% by weight polyethylene glycol (300 MW), and 0.1-2% by weight bioactive glass.

In some exemplary scenarios, the Paste A (Paste A5) comprises about 25% by weight magnesium oxide calcined (heat treated) by weight, 0.1-1% by weight calcium hydroxide, 48-49.9% by weight zirconium oxide, 25% by weight polyethylene glycol (300 MW), 0.1-2% bioactive glass, and 0.001-0.005% by weight Halloysite clay/chlorohexidine/benzalkonium chloride/benzethonium chloride.

In some preferred exemplary scenarios, the Paste A (Paste A6) comprises about 25% by weight magnesium oxide calcined (heat treated) by weight, 0.1-1% by weight calcium hydroxide, 48-49.9% by weight zirconium oxide, 25% by weight polyethylene glycol (300 MW), 0.1-2% bioactive glass, 0.001-0.005% by weight halloysite clay/chlorohexidine/benzalkonium chloride/benzethonium chloride, and 0.001-0.005% hydroxyapatite nanopowder.

In an embodiment of the present invention, the Paste B is a mixture comprising phosphates, polyanionic polymers, cement setting modulators, host-inclusion particles, antimicrobial agents, and radiopacity agents suspended in a non-aqueous liquid carrier.

In an embodiment of the present invention, the polyanionic polymers can include, but not restricted to, polyamidoamine carboxylate/sulfonic (PANAM) dendrimers, polyanionic dendrimers (having any reactive anionic groups), polyacrylic acid, and the like, or combinations thereof. The polyanionic polymers serving as a lattice for remineralizing agents to integrate with the existing bone or tooth.

In an embodiment of the present invention, the polyanionic polymers serve as nucleation sites for the sequestering of remineralizing ions via electrostatic interactions. More specifically, they serve to direct and concentrate therapeutic or remineralizing ions similar to the action of dentin phosphoprotein and other proteins involved in the remineralization of dentin in developing teeth. This "biomimetic" action results in the active and guided remineralization and reinforcement of an endodontically treated tooth. Moreover, the "biomimetic" action is capable of remineralizing and minimizing damage caused by instrumentation/canal shaping process, such as microfractures and the like.

In an embodiment of the present invention, the cement setting modulators can include, but not restricted to, calcium chloride, monobasic calcium phosphate, calcium hydroxide, and the like, or combinations thereof.

In an embodiment of the present invention, the liquid carrier can include an ionic liquid, a non-aqueous hydrophilic solvent, and combinations thereof. The ionic liquid can include, but not restricted to, tetrafluoroborates such as 1-Butyl-3-methylimidazolium tetrafluoroborate (Bmim+ BF4), and the like, or combinations thereof. The ionic liquid aids in catalyzing the biomimetic remineralization reaction. The non-aqueous hydrophilic solvent can include, but not restricted to, glycerol, glycerin, polyethylene glycol, ethanol (EtOH) dimethyl sulfoxide (DMSO), and the like, or combinations thereof. In some preferred embodiments, the liquid carrier is polyethylene glycol of 300 MW, other molecular weights are contemplated and do not depart from the scope of the invention.

In an exemplary scenario, the Paste B (Paste B1) is a mixture comprising a blend of bioactive glass 45S5, mesoporous silica and/or silver nanoparticles, β-tricalcium phosphate, monobasic calcium phosphate, polyamidoamine carboxylate/sulfonic (PANAM) dendrimers, hydroxyapatite, sodium borate and calcium chloride suspended in a liquid carrier.

In an exemplary scenario, the Paste B (Paste B2) is a mixture comprising a blend of bioactive glass 45S5, mesoporous silica and/or silver nanoparticles, monobasic calcium phosphate ytterbium trifluoride and/or niobium oxide, β-tricalcium phosphate, polyamidoamine carboxylate (PANAM) dendrimers, and hydroxyapatite suspended in a liquid carrier.

In an exemplary scenario, the Paste B (Paste B3) is a mixture comprising a blend of bioactive glass 45S5, mesoporous silica and/or silver nanoparticles, ytterbium trifluoride and/or niobium oxide, monobasic calcium phosphate, β-tricalcium phosphate, polyamidoamine carboxylate (PANAM) dendrimers, hydroxyapatite, and calcium chloride suspended in a liquid carrier.

In an exemplary scenario, the Paste B (Paste B4) is a mixture comprising about 3-13% by weight bioactive glass 45S5, about 3-13% by weight mesoporous silica and/or silver nanoparticles, about 3-13% by monobasic calcium phosphate, about 0.3-3% polyamidoamine carboxylate (PANAM) dendrimers, about 0.1-7% by weight hydroxyapatite, about 0.5-7% by weight calcium chloride, and 30-70% 1-Butyl-3-methylimidazolium tetrafluoroborate (Bmim+ BF4).

In an exemplary scenario, the Paste B (Paste B5) is a mixture comprising about 3-13% by weight bioactive glass 45S5, about 3-13% by weight mesoporous silica and/or silver nanoparticles, about 3-13% by weight β-tricalcium phosphate, about 0.3-3% polyamidoamine carboxylate/sulfonic (PANAM) dendrimers, about 0.1-7% by weight hydroxyapatite, about 0.5-7% by weight calcium chloride, and 30-70% dimethyl sulfoxide (DMSO).

In another exemplary scenario, the Paste B (Paste B6) is a mixture comprising about 10-26% monobasic calcium phosphate (milled to 3-10 μm), 50-60% zirconium oxide, and 25% polyethylene glycol (300 MW).

In yet another exemplary scenario, the Paste B (Paste B7) is a mixture comprising about 10-26% monobasic calcium phosphate (milled to 3-10 μm), 50-60% zirconium oxide, 25% polyethylene glycol (300 MW), and 0.001-0.005% polyacrylic acid or PAMAM dendrimeric polymers.

In an exemplary scenario, the Paste B (Paste B8) is a mixture comprising about 10-26% monobasic calcium phosphate (milled to 3-10 μm), 50-60% zirconium oxide, 25% polyethylene glycol (300 MW), and 0.001-0.005% halloysite clay/chlorohexidine/benzalkonium chloride/benzethonium chloride.

In an exemplary scenario, the Paste B (Paste B9) is a mixture comprising about 10-26% monobasic calcium phosphate (milled to 10 μm), 50-60% zirconium oxide, 25% polyethylene glycol (300 MW), 0.001-0.005% polyacrylic acid or PAMAM dendrimeric polymers, and 0.00001-0.00005% halloysite clay/chlorohexidine/benzalkonium chloride/benzethonium chloride.

In a preferred exemplary scenario, Paste B (Paste B10) is a mixture comprising about 12% monobasic calcium phosphate (milled to 3-10 μm), 60-63% zirconium oxide, 25% polyethylene glycol (300 MW), 0.001-0.005% polyacrylic acid or PAMAM dendrimeric polymers, and 0.00001-0.005% halloysite clay/chlorohexidine/benzalkonium chloride/benzethonium chloride.

In an embodiment of the present invention, the endodontic cement composition enhances the lifetime of a dental restoration.

In an embodiment of the present invention, the endodontic cement composition is provided in a syringe.

In an embodiment of the present invention, the syringe may have one or more barrels and a mixing tip.

In an embodiment of the present invention, the paste A is loaded in a first barrel of the syringe and the paste B is loaded in a second barrel of the syringe.

In an embodiment of the present invention, the paste A is loaded in a first barrel of the syringe and the paste B is loaded in a second barrel of the syringe, wherein the paste A is a pozzolanic cementitious mineral paste and the paste B is a mixture comprising polyanionic polymers, cement setting modulators, host-inclusion particles, bioactive glasses, and radiopacity agents suspended in a liquid carrier.

In an embodiment of the present invention, the paste A and the paste B are mixed through a mixing tip upon extrusion directly into a dental site.

In an embodiment of the present invention, the dental site can be a root canal of a tooth.

In an embodiment of the present invention, the paste A and paste B upon mixing and placing directly into the root canal, the mixture thus formed is hydrated by absorbing moisture from oral environment and seals the tooth. The moisture may be absorbed from saliva present in the oral environment.

In an embodiment of the present invention, calcium hydroxide is formed during hydration of the mixture, particularly of the pozzolanic cementitious material, which generates a variety of ions and initiates the remineralizing effect.

In an embodiment of the present invention, a method of preparing an endodontic cement composition is provided. The method comprises mixing of a Paste A and a Paste B, wherein the Paste A is an alkaline pozzolanic cementitious mineral paste and the Paste B is an acidic mixture comprising monobasic calcium phosphate, polyanionic polymers, cement setting modulators, the endodontic cement composition additionally comprising host-inclusion particles, bioactive glasses, and radiopacity agents suspended in a liquid carrier.

In an embodiment of the present invention, a method of preparing an endodontic cement composition is provided. The method comprises mixing of a Paste A and a Paste B, wherein the Paste A is an alkaline pozzolanic cementitious mineral paste comprising a blend of aluminates and calcined clays suspended in a liquid carrier and the Paste B is an acidic mixture comprising polyanionic polymers, cement setting modulators, the endodontic cement composition additionally comprising host-inclusion particles, bioactive glasses, and radiopacity agents suspended in a liquid carrier.

In an embodiment of the present invention, a method of preparing an endodontic cement composition is provided. The method comprises mixing of a Paste A and a Paste B, wherein the Paste A is an alkaline pozzolanic cementitious mineral paste comprising a blend of pozzolanic cementitious material, calcium hydroxide, sodium phosphate, ammonium phosphate, potassium phosphate, and magnesium oxide and/or calcium oxide suspended in a liquid carrier and the Paste B is an acidic mixture comprising polyanionic polymers, cement setting modulators, the endodontic cement composition additionally comprising host-inclusion particles, bioactive glasses, and radiopacity agents suspended in a liquid carrier.

In an embodiment of the present invention, a method of preparing an endodontic cement composition is provided. The method comprises mixing of a Paste A and a Paste B, wherein the Paste A is an alkaline pozzolanic cementitious mineral paste comprising a blend of pozzolanic cementitious material, calcium hydroxide, calcium chloride, sodium phosphate, ammonium phosphate, potassium phosphate, magnesium oxide and/or calcium oxide, and radiopacity agents suspended in a liquid carrier and the Paste B is an acidic mixture comprising polyanionic polymers, cement setting modulators, the endodontic cement composition additionally comprising host-inclusion particles, bioactive glasses, and radiopacity agents suspended in a liquid carrier.

In an embodiment of the present invention, a method of preparing an endodontic cement composition is provided. The method comprises mixing of a Paste A and a Paste B, wherein the Paste A is an alkaline pozzolanic cementitious mineral paste comprising a blend of pozzolanic cementitious material, calcium hydroxide, magnesium oxide and/or calcium oxide, and radiopacity agents suspended in a liquid carrier and the Paste B is an acidic mixture comprising polyanionic polymers, cement setting modulators, the endodontic cement composition additionally comprising host-inclusion particles, bioactive glasses, and radiopacity agents suspended in a liquid carrier.

In an embodiment of the present invention, a method of preparing an endodontic cement composition is provided. The method comprises mixing of a Paste A and a Paste B, wherein the Paste A is an alkaline pozzolanic cementitious mineral paste and the Paste B is an acidic mixture comprising a blend of bioactive glass 45S5, mesoporous silica and/or silver nanoparticles, β-tricalcium phosphate, polyamidoamine carboxylate/sulfonic (PANAM) dendrimers, polyacrylic acid, hydroxyapatite, and calcium chloride suspended in a liquid carrier.

In an embodiment of the present invention, a method of preparing an endodontic cement composition is provided. The method comprises mixing of a Paste A and a Paste B, wherein the Paste A is an alkaline pozzolanic cementitious mineral paste and the Paste B is an acidic mixture comprising a blend of bioactive glass 45S5, mesoporous silica and/or silver nanoparticles, ytterbium trifluoride and/or niobium oxide, β-tricalcium phosphate, polyamidoamine carboxylate/sulfonic (PANAM) dendrimers, and hydroxyapatite suspended in a liquid carrier.

In an embodiment of the present invention, a method of preparing an endodontic cement composition is provided. The method comprises mixing of a Paste A and a Paste B, wherein the Paste A is an alkaline pozzolanic cementitious mineral paste and the Paste B is a mixture comprising a blend of bioactive glass 45S5, mesoporous silica and/or silver nanoparticles, ytterbium trifluoride and/or niobium oxide, β-tricalcium phosphate, polyamidoamine carboxylate/sulfonic (PANAM) dendrimers, hydroxyapatite, and calcium chloride suspended in a liquid carrier.

In an embodiment of the present invention, a method of treating a patient in need of an endodontic treatment is provided. The method comprises the following steps: (a) forming an endodontic cement by mixing a Paste A and a Paste B, wherein the Paste A is an alkaline pozzolanic cementitious mineral paste comprising a blend of aluminates and calcined clays suspended in a liquid carrier and the Paste B is an acidic mixture comprising polyanionic polymers, cement setting modulators, host-inclusion particles, bioactive glasses, and radiopacity agents suspended in a liquid carrier, and wherein the mixing is done upon extrusion through a mixing tip of a syringe containing paste A and paste B in separate barrels; and (b) delivering the endodontic cement to a dental site in the patient as part of a procedure for the endodontic treatment.

In a preferred embodiment of the present invention, Paste A6 is mixed with Paste B10 to create a biomimentic, actively remineralizing, radiopaque, antimicrobial endodontic cement.

In a preferred embodiment of the present invention, a method of treating a patient in need of an endodontic treatment is provided. The method comprises the following steps: (a) forming an endodontic cement by mixing a Paste A and a Paste B, wherein the Paste A is an alkaline pozzolanic cementitious mineral paste comprising a blend of magnesium oxide, calcium oxide, zirconium oxide, bioactive glass, and host-inclusion agents with antimicrobial compounds suspended in a non-aqueous hydrophilic carrier and the Paste B is an acidic mixture comprising polyanionic polymers, cement setting modulators, host-inclusion particles with antimicrobial compounds, and radiopacity agents suspended in a non-aqueous hydrophilic carrier, and wherein the mixing is done upon extrusion through a mixing tip of a syringe containing paste A and paste B in separate barrels; and (b) delivering the endodontic cement to a dental site in the patient as part of a procedure for the endodontic treatment.

EXAMPLES

Example 1: Preparing the Endodontic Cement Composition

The endodontic cement composition of the present invention is prepared by mixing a Paste A and a Paste B in a dual barrel syringe while directly placing the endodontic cement on a root canal. The Paste A prepared by mixing the components mentioned in Table 1 and is added to one barrel of the syringe. Similarly, the Paste B prepared by mixing the components mentioned in Table 2 is added to the other barrel of the syringe.

TABLE 1

Exemplary composition of Paste A

| Components | w/w percentage of the component in paste A |
|---|---|
| Magnesium Oxide (calcined, heat treated) | 25% |
| Calcium Hydroxide | 0.1-1% |
| Zirconium Oxide | 48% |
| Polyethylene Glycol (300 MW) | 25% |
| Bioactive Glass | 0.1-2% |
| Halloysite clay/chlorohexidine/benzalkonium chloride/benzethonium chloride | 0.00001-0.005% |

TABLE 2

Exemplary composition of Paste B

| Components | w/w percentage of the component in paste B |
|---|---|
| Monobasic calcium phosphate (milled to 10 μm) | 12% |
| Zirconium oxide | 60-63% |
| Polyethylene glycol | 25% |
| Halloysite clay/chlorohexidine/benzalkonium chloride/benzethonium chloride | 0.00001-0.005% |
| Polyacrylic acid or PAMAM dedrimeric polymers | 0.001-0.005% |

Upon adding the Paste A and Paste B separately in the barrels of the syringe, the syringe is positioned on a root canal of a tooth and mixing of the Paste A and the Paste B occurs through a mixing tip upon extrusion directly into the root canal. The mixture thus formed is then hydrated by absorbing moisture from oral environment to seal the tooth. The moisture may be absorbed from saliva present in the oral environment.

Therefore, the present invention provides a biomimetic endodontic cement composition comprising two different pastes, namely, Paste A and Paste B. The Paste A is a is a alkaline pozzolanic cementitious mineral paste and the Paste B is an acidic mixture comprising polyanionic polymers, cement setting modulators, the endodontic cement composition additionally comprising host-inclusion particles, bioactive glasses, and radiopacity agents suspended in a liquid carrier. The endodontic cement composition actively mimics and accelerates the naturally-biologically occurring remineralization mechanisms in dentition or teeth. The endodontic cement composition provides sustained disinfection or prophylaxis that prevents re-infiltration of bacteria in the dentition/tooth and enhances the lifetime of a dental restoration.

Moreover, any of the embodiments of Paste A may be mixed with any of the embodiments of Paste B to form a biomimetic endodontic cement composition.

Example 2: pH of the Biomimetic Endodontic Cement Composition Relative to Known Materials Cements were carefully placed in polyethylene tubes measuring 1.0 mm in diameter and 10.0 mm in length with only one open end. Five samples were used for each material. After being filled and weighed, each specimen was immediately immersed in test glass tubes containing 10 ml of distilled water which were then sealed with laboratory film and placed in an incubated at 37° C. throughout the study period. The pH was measured using a pH meter previously calibrated with solution standards of known pH (4, 7, & 10).

TABLE 3 pH over time wherein EDS is the biomimetic endodontic cement

| Sealer | 3 hours | 24 hours | 72 hours | 168 hours | 240 Hours |
|---|---|---|---|---|---|
| BC Sealer | 10.21 | 11.21 | 11.62 | 12.11 | 11.16 |
| EDS Sealer | 9.51 | 11.11 | 11.41 | 11.25 | 11.12 |
| EZ-Fill Express (epoxy) | 8.0 | 7.77 | 7.82 | 7.67 | 7.71 |
| Control* | 6.9 | 6.9 | 6.9 | 6.9 | 6.9 |

*Deionized water was used as a control along with all other groups. Average pH values shown (n = 5)

The primary reaction from the mixing of an exemplary Paste A (magnesium oxide) and Paste B (monobasic calcium phosphate):

$$6MgO + 3Ca(H_2PO_4)_2 \rightarrow 2Mg_3(PO_4)_2 + 6H_2O$$

The precipitation reaction of calcium phosphate apatite:

$$10Ca^{2+} + 6PO_4^{3-} + 2OH^- \rightarrow Ca_{10}(PO_4)_6(OH)_2$$

Example 3: Preparation and Properties of Calcium Magnesium Phosphate Cement

This example describes the preparation of an injectable general purpose calcium magnesium phosphate cement. The raw materials utilized for the preparation of the CMPC cement were calcined MgO (97% Sigma Aldrich), anhydrous monobasic calcium phosphate (Fischer), and polyethylene glycol (MW 300, Sigma Aldrich). The anhydrous monobasic calcium phosphate was milled to an average particle size of 3.22 μm (Beckman Coulter LS Particle size analyzer) using a Jet mill AFG (Hozokawa Micron Powder Systems). A 100 gram batch of each respective paste was prepared by mixing 75 grams of MgO or monobasic calcium phosphate with 25 grams of PEG and placing in a speed mixer (Flaktek) for 1-2 minutes at 3,500 RPM.

A double barrel syringe was then loaded with each respective paste which was then extruded/mixed through a mixing tip into a cylindrical mold (8 mm diameter, 20 mm height). The mold was then placed submerged in Ringers solution (0.15 M sodium chloride) at 37° C. to simulate physiological conditions. After different periods of time (1 hr, 2 hr, 1 and 7 days) the specimens were removed from the mold and the compressive strength was measured under wet conditions using a material testing machine (MTS). Setting time 4 hours.

Example 4: Preparation and Properties of Radiopaque Calcium Magnesium Phosphate Cement for Dental Applications This example describes the preparation of a radiopaque injectable general purpose calcium magnesium phosphate cement. The raw materials utilized for the preparation of the CMPC cement were calcined MgO (97% Sigma Aldrich), anhydrous monobasic calcium phosphate (Fischer), zirconium oxide (Fischer) and polyethylene glycol (MW 300, Sigma Aldrich). A range of 3 μM to 10 μM and ranges in between are contemplated by embodiments of the present invention for the anhydrous monobasic calcium phosphate. In one embodiment, the anhydrous monobasic calcium phosphate was milled to an average particle size of 3.22 μM (Beckman Coulter LS Particle size analyzer) using a Jet mill AFG (Hozokawa Micron Powder Systems). A 100 gram batch of each respective paste was prepared by mixing 25 grams of MgO or monobasic calcium phosphate with 25 grams of PEG.

The radiopacifying agent zirconium oxide (50 grams) was added to each paste and placed in a speed mixer (Flaktek) for 1-2 minutes at 3,500 RPM. A double barrel syringe was then loaded with each respective paste which was then extruded/ mixed through a mixing tip into a cylindrical mold (8 mm diameter, 20 mm height). The mold was then placed submerged in Ringers solution (0.15 M sodium chloride) at 37° C. to simulate physiological conditions. After different periods of time (1 hr, 2 hr, 1 and 7 days) the specimens were removed from the mold and the compressive strength was measured under wet conditions using a material testing machine (MTS). Radiopacity was found to be about 8.32 mm A1. Setting time is 4-6 hours.

Example 5: Preparation and Properties of Radiopaque Antibacterial Calcium Magnesium Phosphate Cement for Dental Applications This example describes the Preparation of a Radiopaque Injectable General Purpose calcium magnesium phosphate cement. The raw materials utilized for the preparation of the CMPC cement were calcined MgO (97% Sigma Aldrich), anhydrous monobasic calcium phosphate (Fischer), zirconium oxide (Fischer) and polyethylene glycol (MW 300, Sigma Aldrich). The anhydrous monobasic calcium phosphate was milled to an average particle size of 3.22 µm (Beckman Coulter LS Particle size analyzer) using a Jet mill AFG (Hozokawa Micron Powder Systems).

A 100 gram batch of paste A was prepared by mixing 25 grams of MgO, 1 gram of $Ca(OH)_2$, 2 grams of bioactive glass (Schott glass, 45S5 formulation), 47 grams of zirconium oxide (Fischer) and 25 grams of PEG. These materials were placed in a speed mixer (Flaktek) for 1-2 minutes at 3,500 RPM.

Paste B was prepared by placing 15 grams of monobasic calcium phosphate, 60 grams of zirconium oxide with 25 grams of PEG and placed in a speed mixer (Flaktek) for 1-2 minutes at 3,500 RPM. 50 milligrams of Halloysite clay/chlorohexidine host inclusion particles/filler was added to both pastes and subsequently mixed.

A double barrel syringe was then loaded with each respective paste which was then extruded/mixed through a mixing tip into a cylindrical mold (8 mm diameter, 20 mm height). The mold was then placed submerged in Ringers solution (0.15 M sodium chloride) at 37° C. to simulate physiological conditions. After different periods of time (1 hr, 2 hr, 1 and 7 days) the specimens were removed from the mold and the compressive strength was measured under wet conditions using a material testing machine (MTS). Radiopacity was found to be about 8.22 mm A1. Setting time is 4-6 hours.

Example 6: Preparation and Properties of Biomimetic Remineralizing Antibacterial Calcium Phosphate Cement for Dental Applications This example describes the preparation of a radiopaque injectable general purpose calcium magnesium phosphate cement. The raw materials utilized for the preparation of the CMPC cement were calcined MgO (97% Sigma Aldrich), anhydrous monobasic calcium phosphate (Fischer), zirconium oxide (Fischer) and polyethylene glycol (MW 300, Sigma Aldrich). The anhydrous monobasic calcium phosphate was milled to an average particle size of 3.22 µm (Beckman Coulter LS Particle size analyzer) using a Jet mill AFG (Hozokawa Micron Powder Systems).

A 100 gram batch of paste A was prepared by mixing 25 grams of MgO, 1 gram of $Ca(OH)_2$, 2 grams of bioactive glass (Schott glass, 45S5 formulation), 47 grams of zirconium oxide (Fischer) and 25 grams of PEG. These materials were placed in a speed mixer (Flaktek) for 1-2 minutes at 3,500 RPM.

Paste B was prepared by placing 15 grams of monobasic calcium phosphate, 60 grams of zirconium oxide with 25 grams of PEG and placed in a speed mixer (Flaktek) for 1-2 minutes at 3,500 RPM. 50 milligrams of halloysite clay/chlorohexidine or halloysite clay/benzalkonium chloride host inclusion particles/filler was added to both pastes and subsequently mixed. As an example of a biomimetic polymer, 500 µg of polyacrylic acid was added to paste B.

A double barrel syringe was then loaded with each respective paste which was then extruded/mixed through a mixing tip into a cylindrical mold (8 mm diameter, 20 mm height). The mold was then placed submerged in Ringers solution (0.15 M sodium chloride) at 37° C. to simulate physiological conditions. After different periods of time (1 hr, 2 hr, 1 and 7 days) the specimens were removed from the mold and the compressive strength was measured under wet conditions using a material testing machine (MTS). Radiopacity was found to be about 8.02 mm A1. Setting time is 4-6 hours.

Although the present invention describes components, compositions and functions implemented in the embodiments with reference to particular standards and protocols, it is not limited to such standards and protocols. Other similar standards and protocols not mentioned herein are in existence and considered to be included in the present invention. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present invention.

The present invention, in various embodiments, and aspects, includes components, compositions, methods, processes, systems and/or apparatus substantially as depicted and described herein, including various embodiments, sub-combinations, and subsets thereof. Those of skill in the art will understand how to make and use the present invention after understanding the present disclosure. The present invention, in various embodiments, and aspects, includes providing compositions, formulations, and processes in the absence of items not described herein or in various embodiments, aspects hereof, including in the absence of such items as may have been used in previous compositions, formulations or processes, e.g., for improving performance, achieving ease and/or reducing cost of preparation.

The foregoing discussion of the present invention has been presented for purposes of illustration and description. It is not intended to limit the present invention to the form or forms disclosed herein. In the foregoing Detailed Description, for example, various features of the present invention are grouped together in one or more embodiments, or aspects for the purpose of streamlining the disclosure. The features of the embodiments, or aspects may be combined in alternate embodiments, or aspects other than those discussed above. This method of disclosure is not to be interpreted as reflecting an intention the present invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate embodiment of the present invention.

Moreover, though the description of the present invention has included description of one or more embodiments, or aspects and certain variations and modifications, other variations, combinations, and modifications are within the scope of the present invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, components, functions, ranges or steps to those claimed, whether or not such alternate, interchangeable and/or equivalent structures, components, functions, ranges or steps are disclosed herein, and without intending to publicly dedicate any patentable subject matter.

I claim:

1. An endodontic cement comprising:
a Paste A, Paste A being a pozzolanic and alkaline mixture of calcined and heat treated magnesium oxide, calcium silicate, dicalcium silicate, tricalcium silicate, metakaolin, calcium hydroxide and zirconium oxide, said mixture in solution with a non-aqueous hydrophilic carrier;
a Paste B, Paste B being acidic and being capable of modulating cement setting, Paste B comprising a mixture of milled monobasic calcium phosphate, zirconium oxide, wherein said mixture is in solution with the non-aqueous hydrophilic carrier; and
wherein a mixture of Paste A and Paste B hydrates in an aqueous environment to form the endodontic cement, the endodontic cement being radiopaque and antimicrobial when created.

2. The endodontic cement of claim 1, wherein Paste A further comprises bioactive glass.

3. The endodontic cement of claim 1, wherein Paste A further comprises host-inclusion particles.

4. The endodontic cement of claim 3, wherein the host-inclusion particles are halloysite clay.

5. The endodontic cement of claim 3, wherein the host-inclusion particles are impregnated with antimicrobial compounds.

6. The endodontic cement of claim 1, wherein Paste A further comprises hydroxyapatite nanopowder.

7. The endodontic cement of claim 1, wherein Paste B further comprises host-inclusion agents.

8. The endodontic cement of claim 7, wherein the host-inclusion particles are halloysite clay.

9. The endodontic cement of claim 7, wherein the host-inclusion particles are impregnated with antimicrobial compounds.

10. The endodontic cement of claim 1, wherein Paste B further comprises polyacrylic acid or PAMAM dendrimeric polymers.

11. A biomimetic endodontic cement comprising:
a Paste A, Paste A comprising, by weight, about 23-27% calcined and heat treated magnesium oxide, 0.08-1.2% calcium hydroxide, 47-51% zircondium oxide, and 0.08-2.2% bioactive glass in a non-aqueous hydrophilic carrier at about 24-26% by weight; and
a Paste B, Paste B comprising 8-28% milled monobasic calcium phosphate, 50-60% zirconium oxide, 0.001-0.005% polyacrylic acid or PAMAM dendrimeric polymers in a non-aqueous hydrophilic carrier at about 24-26% by weight;
wherein a mixture of Paste A and Paste B hydrolyzes in an aqueous environment to form the biomimetic endodontic cement, the endodontic cement being biomimetic, radiopaque, and antimicrobial.

12. The biomimetic endodontic cement of claim 11, wherein Paste A further comprises host-inclusion particles.

13. The biomimetic endodontic cement of claim 12, wherein the host-inclusion particles are halloysite clay.

14. The biomimetic endodontic cement of claim 12, wherein the host-inclusion particles are impregnated with antimicrobial compounds.

15. The biomimetic endodontic cement of claim 14, wherein the antimicrobial agents are chlorohexidine, benzalkonium chloride, or benzethonium chloride.

16. The biomimetic endodontic cement of claim 11, wherein the non-aqueous liquid carrier is polyethylene glycol.

17. The biomimetic endodontic cement of claim 11, wherein the mixture of Paste A and Paste B is injected into the exposed root canal of a tooth.

18. A biomimetic endodontic cement comprising:
a Paste A, Paste A comprising by weight about 25% calcined and heat treated magnesium oxide, 0.1-1% calcium hydroxide, 48% zirconium oxide, 25% polyethylene glycol, 0.1-2% bioactive glass, and 0.001-0.005% halloysite clay/chlorohexidine/benzalkonium chloride/benzethonium chloride; and
a Paste B, Paste B comprising by weight about 12% milled monobasic calcium phosphate, 60-63% zirconium oxide, 25% polyethylene glycol, 0.00001-0.00005% halloysite clay/chlorohexidine/benzalkonium chloride/benzethonium chloride, and 0.001-0.005% polyacrylic acid or PAMAM dendrimeric polymers;
wherein Paste A and Paste B remain separated until use and wherein a mixture of Paste A and Paste B will hydrate in an aqueous environment, creating a robust biomimetic, radiopaque, antimicrobial, and actively remineralizing endodontic cement.

19. The biomimetic endodontic cement of claim 18, wherein the polyethylene glycol is 300 molecular weight.

20. The biomimetic endodontic cement of claim 18, wherein the milled monobasic calcium phosphate is milled to 3-10 μm.

21. The biomimetic endodontic cement of claim 18, wherein the mixture of Paste A and Paste B is injected into the exposed root canal of a tooth.

* * * * *

UNITED STATES PATENT AND TRADEMARK OFFICE
CERTIFICATE OF CORRECTION

PATENT NO. : 10,105,289 B2
APPLICATION NO. : 15/590931
DATED : October 23, 2018
INVENTOR(S) : Jason Edward Guzman Page 1 of 1

It is certified that error appears in the above-identified patent and that said Letters Patent is hereby corrected as shown below:

In the Claims

In Column 15, in Claim 7, Line 35, please replace "agents" with -- particles --.

In Column 16, in Claim 15, Line 16, please replace "agents" with -- compounds --.

Signed and Sealed this
Fifteenth Day of January, 2019

Andrei Iancu
*Director of the United States Patent and Trademark Office*